(12) United States Patent
Waisman et al.

(10) Patent No.: US 10,744,304 B2
(45) Date of Patent: Aug. 18, 2020

(54) INVERTED BALLOON NECK ON CATHETER

(71) Applicant: BOSTON SCIENTIFIC LIMITED, Hamilton (BM)

(72) Inventors: Lea Waisman, Karkur (IL); Boaz Manash, Givat Ada (IL); Dan Rottenberg, Haifa (IL); Abi Zakay, Zichron Yacov (IL)

(73) Assignee: BOSTON SCIENTIFIC LIMITED, Hamilton (BM)

(*) Notice: Subject to any disclaimer, the term of this patent is extended or adjusted under 35 U.S.C. 154(b) by 516 days.

(21) Appl. No.: 14/924,257

(22) Filed: Oct. 27, 2015

(65) Prior Publication Data

US 2016/0045713 A1 Feb. 18, 2016

Related U.S. Application Data

(63) Continuation of application No. 13/392,229, filed as application No. PCT/US2010/046744 on Aug. 26, 2010, now abandoned.

(Continued)

(51) Int. Cl.
*A61M 25/01* (2006.01)
*A61M 25/10* (2013.01)
(Continued)

(52) U.S. Cl.
CPC ......... *A61M 25/0194* (2013.01); *A61B 17/22* (2013.01); *A61M 25/10* (2013.01);
(Continued)

(58) Field of Classification Search
CPC .............. A61M 25/0194; A61M 25/10; A61M 2025/0197; A61M 17/22; A61M 25/104;
(Continued)

(56) References Cited

U.S. PATENT DOCUMENTS 2,730,161 A 1/1956 Langer
3,833,004 A 9/1974 Vazquez et al.
(Continued)

FOREIGN PATENT DOCUMENTS

EP 0314970 A1 5/1989
EP 0359489 A2 3/1990
(Continued)

OTHER PUBLICATIONS

Belli et al., "Peripheral Vascular Occlusions: Mechanical Recanalization with a Metal Laser Probe After Guide Wire Dissection" Radiology, vol. 176(2): 539-541, Aug. 1990.
(Continued)

*Primary Examiner* — Erich G Herbermann
(74) *Attorney, Agent, or Firm* — Seager, Tufte & Wickhem LLP (57) ABSTRACT

A method for thermal bonding of an inverted balloon neck on a catheter, including placing an inverted balloon neck (84) on a shaft (86) of a catheter, and characterized by applying heat at an internal hollow (85) of the shaft (86) where the inverted balloon neck (84) is placed, while applying internal pressure to attach an external surface of the shaft (86) to the inverted balloon neck (84).

20 Claims, 6 Drawing Sheets

Related U.S. Application Data (60) Provisional application No. 61/275,324, filed on Aug. 28, 2009, provisional application No. 61/275,323, filed on Aug. 28, 2009.

(51) Int. Cl.
*A61B 17/22* (2006.01)
*A61M 25/00* (2006.01)

(52) U.S. Cl.
CPC ...... *A61M 25/104* (2013.01); *A61M 25/1006* (2013.01); *A61M 25/1027* (2013.01); *A61M 25/1034* (2013.01); *A61B 2017/22051* (2013.01); *A61B 2017/22095* (2013.01); *A61M 25/0054* (2013.01); *A61M 2025/0197* (2013.01); *A61M 2025/1065* (2013.01); *A61M 2025/1093* (2013.01)

(58) Field of Classification Search
CPC .......... A61M 25/1006; A61M 25/1034; A61M 25/1027; A61M 25/0054; A61M 2025/1065; A61M 2025/1093; A61B 2017/22051; A61B 2017/22095
See application file for complete search history.

(56) References Cited

U.S. PATENT DOCUMENTS

| | | |
|---|---|---|
| 4,271,839 A | 6/1981 | Fogarty et al. |
| 4,299,226 A | 11/1981 | Banka |
| 4,630,609 A | 12/1986 | Chin |
| 4,661,095 A | 4/1987 | Taller et al. |
| 4,758,221 A | 7/1988 | Jureidini |
| 4,863,424 A | 9/1989 | Blake, III et al. |
| 4,927,412 A | 5/1990 | Menasche |
| 4,976,710 A | 12/1990 | Mackin |
| 4,990,138 A | 2/1991 | Bacich et al. |
| 5,074,845 A | 12/1991 | Miraki et al. |
| 5,092,848 A | 3/1992 | deCiutiis |
| 5,109,830 A | 5/1992 | Cho |
| 5,163,989 A | 11/1992 | Campbell et al. |
| 5,250,069 A | 10/1993 | Nobuyoshi et al. |
| 5,336,176 A | 8/1994 | Yoon |
| 5,423,846 A | 6/1995 | Fischell |
| 5,514,153 A | 5/1996 | Bonutti |
| 5,522,832 A | 6/1996 | Kugo et al. |
| 5,601,588 A | 2/1997 | Tonomura et al. |
| 5,607,435 A | 3/1997 | Sachdeva et al. |
| 5,628,761 A | 5/1997 | Rizik |
| 5,667,520 A | 9/1997 | Bonutti |
| 5,830,222 A | 11/1998 | Makower |
| 5,860,997 A | 1/1999 | Bonutti |
| 5,916,194 A | 6/1999 | Jacobsen et al. |
| 5,935,108 A | 8/1999 | Katoh et al. |
| 5,938,671 A | 8/1999 | Katoh et al. |
| 5,968,064 A | 10/1999 | Selmon et al. |
| 5,997,503 A | 12/1999 | Willis et al. |
| 6,010,449 A | 1/2000 | Selmon et al. |
| 6,068,638 A | 5/2000 | Makower |
| 6,081,738 A | 6/2000 | Hinohara et al. |
| 6,120,516 A | 9/2000 | Selmon et al. |
| 6,159,225 A | 12/2000 | Makower |
| 6,190,353 B1 | 2/2001 | Makower et al. |
| 6,206,868 B1 | 3/2001 | Parodi |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,261,304 B1 | 7/2001 | Hall et al. |
| 6,264,631 B1 | 7/2001 | Willis et al. |
| 6,283,951 B1 | 9/2001 | Flaherty et al. |
| 6,283,983 B1 | 9/2001 | Makower et al. |
| 6,302,875 B1 | 10/2001 | Makower et al. |
| 6,330,884 B1 | 12/2001 | Kim |
| 6,375,615 B1 | 4/2002 | Flaherty et al. |
| 6,387,119 B2 | 5/2002 | Wolf et al. |
| 6,398,798 B2 | 6/2002 | Selmon et al. |
| 6,423,032 B2 | 7/2002 | Parodi |
| 6,432,127 B1 | 8/2002 | Kim et al. |
| 6,464,665 B1 | 10/2002 | Heuser |
| 6,506,178 B1 | 1/2003 | Schubart et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,519,225 B1 | 2/2003 | Angle et al. |
| 6,533,753 B1 | 3/2003 | Haarstad et al. |
| 6,544,230 B1 | 4/2003 | Flaherty et al. |
| 6,579,302 B2 | 6/2003 | Duerig et al. |
| 6,579,311 B1 | 6/2003 | Makower |
| 6,599,304 B1 | 7/2003 | Selmon et al. |
| 6,602,241 B2 | 8/2003 | Makower et al. |
| 6,613,081 B2 | 9/2003 | Kim et al. |
| 6,616,675 B1 | 9/2003 | Evard et al. |
| 6,632,184 B1 | 10/2003 | Truwit |
| 6,638,247 B1 | 10/2003 | Selmon et al. |
| 6,638,293 B1 | 10/2003 | Makower et al. |
| 6,655,386 B1 | 12/2003 | Makower et al. |
| 6,660,024 B1 | 12/2003 | Flaherty et al. |
| 6,663,577 B2 | 12/2003 | Jen et al. |
| 6,685,648 B2 | 2/2004 | Flaherty et al. |
| 6,694,983 B2 | 2/2004 | Wolf et al. |
| 6,709,444 B1 | 3/2004 | Makower |
| 6,719,725 B2 | 4/2004 | Milo et al. |
| 6,726,677 B1 | 4/2004 | Flaherty et al. |
| 6,746,464 B1 | 6/2004 | Makower |
| 6,900,417 B2 | 5/2005 | Randall |
| 6,916,307 B2 | 7/2005 | Willis et al. |
| 6,955,175 B2 | 10/2005 | Stevens et al. |
| 6,960,222 B2 | 11/2005 | Vo et al. |
| 6,979,290 B2 * | 12/2005 | Mourlas ............ A61B 1/00082 600/104 |
| 7,004,173 B2 | 2/2006 | Sparks et al. |
| 7,059,330 B1 | 6/2006 | Makower et al. |
| 7,094,230 B2 | 8/2006 | Flaherty et al. |
| 7,134,438 B2 | 11/2006 | Makower et al. |
| 7,159,592 B1 | 1/2007 | Makower et al. |
| 7,179,270 B2 | 2/2007 | Makower |
| 7,229,421 B2 | 6/2007 | Jen et al. |
| 7,303,571 B2 | 12/2007 | Makower et al. |
| 7,316,655 B2 | 1/2008 | Garibotto et al. |
| 7,357,794 B2 | 4/2008 | Makower et al. |
| 7,407,506 B2 | 8/2008 | Makower |
| 7,534,204 B2 | 5/2009 | Starksen et al. |
| 7,637,870 B2 | 12/2009 | Flaherty et al. |
| 7,648,517 B2 | 1/2010 | Makower et al. |
| 7,670,329 B2 | 3/2010 | Flaherty et al. |
| 7,729,738 B2 | 6/2010 | Flaherty et al. |
| 7,740,623 B2 | 6/2010 | Nayak et al. |
| 7,846,172 B2 | 12/2010 | Makower |
| 7,849,860 B2 | 12/2010 | Makower et al. |
| 8,574,283 B1 * | 11/2013 | Kamat ................ A61F 2/954 606/191 |
| 2001/0000041 A1 | 3/2001 | Selmon et al. |
| 2001/0012924 A1 | 8/2001 | Milo et al. |
| 2002/0103459 A1 | 8/2002 | Sparks et al. |
| 2002/0128677 A1 | 9/2002 | Duerig et al. |
| 2003/0023204 A1 | 1/2003 | Vo et al. |
| 2003/0109809 A1 | 6/2003 | Jen et al. |
| 2003/0120195 A1 | 6/2003 | Milo et al. |
| 2003/0139763 A1 | 7/2003 | Duerig et al. |
| 2003/0183966 A1 | 10/2003 | Wang et al. |
| 2003/0187494 A1 * | 10/2003 | Loaldi ............... A61F 2/856 623/1.11 |
| 2003/0208156 A1 | 11/2003 | Pham et al. |
| 2003/0226631 A1 | 12/2003 | Sterud et al. |
| 2003/0236542 A1 | 12/2003 | Makower |
| 2004/0133225 A1 | 7/2004 | Makower |
| 2004/0167554 A1 | 8/2004 | Simpson et al. |
| 2004/0230219 A1 | 11/2004 | Roucher, Jr. |
| 2005/0038467 A1 | 2/2005 | Hebert et al. |

(56) References Cited

U.S. PATENT DOCUMENTS

| | | |
|---|---|---|
| 2005/0171478 A1 | 8/2005 | Selmon et al. |
| 2006/0094930 A1 | 5/2006 | Sparks et al. |
| 2006/0184011 A1 | 8/2006 | Macaulay et al. |
| 2006/0271090 A1* | 11/2006 | Shaked ............ A61B 17/12022 606/192 |
| 2006/0276749 A1 | 12/2006 | Selmon et al. |
| 2007/0093779 A1 | 4/2007 | Kugler et al. |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0106320 A1 | 5/2007 | Blix et al. |
| 2007/0265596 A1 | 11/2007 | Jen et al. |
| 2008/0033423 A1 | 2/2008 | Peacock, III |
| 2008/0045996 A1 | 2/2008 | Makower et al. |
| 2008/0125748 A1 | 5/2008 | Patel |
| 2008/0125760 A1 | 5/2008 | Gilboa |
| 2008/0200896 A1 | 8/2008 | Shmulewitz et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2008/0249397 A1 | 10/2008 | Kapadia |
| 2009/0005755 A1 | 1/2009 | Keith et al. |
| 2009/0088685 A1 | 4/2009 | Kugler et al. |
| 2009/0093791 A1 | 4/2009 | Heuser |
| 2009/0124899 A1 | 5/2009 | Jacobs et al. |
| 2009/0131785 A1 | 5/2009 | Lee et al. |
| 2009/0209910 A1 | 8/2009 | Kugler et al. |
| 2009/0264826 A1 | 10/2009 | Thompson |
| 2009/0292296 A1 | 11/2009 | Pansky et al. |
| 2009/0299171 A1 | 12/2009 | Duffy et al. |
| 2009/0299402 A1 | 12/2009 | Orihashi et al. |
| 2010/0063534 A1 | 3/2010 | Kugler et al. |
| 2010/0069945 A1 | 3/2010 | Olson et al. |
| 2010/0094259 A1 | 4/2010 | Makower et al. |
| 2010/0121357 A1 | 5/2010 | Flaherty et al. |
| 2010/0125244 A1 | 5/2010 | McAndrew |
| 2010/0324471 A1 | 12/2010 | Flaherty et al. |

FOREIGN PATENT DOCUMENTS

| | | |
|---|---|---|
| WO | 0176678 A1 | 10/2001 |
| WO | 2006105244 A2 | 10/2006 |
| WO | 2007033052 A2 | 3/2007 |
| WO | 2008120209 A1 | 10/2008 |

OTHER PUBLICATIONS

Bolia et al., "Recanalisation of Femoro-Popliteal Occlusions: Improving Success Rate by Subintimal Recanalisation", Clinical Radiology [The Royal College of Radiologists], vol. 40(3): 325, May 1989.

Bolia et al., "Femoropopliteal and Crural Artery Recanalization Using Subintimal Angioplasty" Seminars in Vascular Surgery, vol. 8(3): 253-264, Sep. 1995.

Bolia et al., "Percutaneous Transluminal Angioplasty of Occlusions of the Femoral and Popliteal Arteries by Subintimal Dissection" CardioVascular and Interventional Radiology, vol. 13(6): 357-363, Nov. 1990.

Bolia, "Percutaneous Intentional Extraluminal (subintimal) recanalization of crural arteries," European Journal of Radiology, vol. 28(2): 199-204, Oct. 1998.

Bolia et al., "Percuntaneous Extraluminal (Subintimal) Recanalization of a Brachial Artery Occlusion Following Cardiac Catheterization," CardioVascular and International Rediology, vol. 19: 184-186, May 1996.

Colombo et al., "Treating Chronic Total Occlusions Using Subintimal Tracking and Reentry: The STAR Technique" Catheterization and Cardiovascular Interventions, vol. 64: 407-411, Apr. 2005.

Jacobs et al., "Crossing Chronic Total Occlusions of the Iliac and Femoral-Popliteal Vessels and the Use of True Lumen Reentry Devices," Perspectives in Vascular Surgery and Endovascular Therapy, vol. 18(1): 31-37, Mar. 2006.

Kimura et al., "Subintimal Wire Position During Angioplasty of a Chronic Total Coronary Occlusion: Detection and Subsequent Procedural Guidance by Intravascular Ultrasound," Catheterization and Cardiovascular Diagnosis, vol. 35 (3): 262-265, Jul. 1995.

Nydahl et al., "Technical Report: Recanalisation of All Three Infrapopliteal Arteries by Subintimal Angioplasty" Clinical Radiology [The Royal College of Radiologists], vol. 51(5):366-367, May 1996.

Rosenthal et al., "Subintimal Dissection and False Tract Formation During Successful Laser Thermal Probe ('Hot Tip') Angioplasty", Journal of Interventional Radiology, vol. 4(1): 19-22, Jan. 1989.

* cited by examiner

INVERTED BALLOON NECK ON CATHETER

CROSS-REFERENCE TO RELATED APPLICATION

This application is a continuation of U.S. patent application Ser. No. 13/392,229, filed on Feb. 24, 2012; which is a 371 of PCT/US2010/046744, filed on Aug. 26, 2010; which claims benefit of 61/275,324, filed Aug. 28, 2009 and claims benefit of 61/275,323, filed Aug. 28, 2009, the contents of which are fully incorporated herein by reference.

FIELD OF THE INVENTION

The present invention relates generally to devices and methods for re-entry into a blood vessel's true lumen from a subintimal space between layers of the blood vessel.

BACKGROUND OF THE INVENTION

Chronic Total Occlusion (CTO) is an arterial vessel blockage that impedes proper blood flow beyond the obstruction. Poor blood flow can lead to insufficient delivery of blood to muscles and vital organs. CTO can occur both in the coronary and peripheral arteries, resulting in disability and even death. The underlying cause of CTO is atherosclerosis.

In order to reverse the effects of CTO, proper blood flow must be reestablished. This must be achieved by either driving through and removing the CTO or creating a bypass around the CTO. Under either scenario, the first step is to "cross" or drive a guidewire through or around the CTO. If the occlusion is relatively new, the plaque is likely to be soft and the guidewire will penetrate and cross the plaque. Thereafter, balloon angioplasty and stenting can be performed. However, if the plaque has been lodged in the vessel for several weeks or months, the plaque can become much harder as the occlusion becomes fibrotic and calcified, making it almost impossible for a guidewire to cross. Failure to cross the obstruction is the primary failure mode for CTO recanalization, and often leads to the abortion of the interventional procedure in favor of a surgical bypass procedure instead, with higher costs and complications.

It is known in the art that when trying to cross an occluded blood vessel with a guidewire, in many cases the guidewire inadvertently deflects into the subintimal space between the intimal layer and the adventitial layer of the blood vessel. Once in the subintimal space, the guidewire can be advanced along side the CTO (which is on the other side of the intimal wall) and beyond the length of the occlusion. Dissection of the blood vessel and guidewire insertion into subintimal space is very common, especially in blocked peripheral blood vessels. The difficulty in many cases is to direct the guidewire back into the blood vessel's true lumen beyond the occlusion so that this new channel can be dilated and used as an internal conduit for blood supply. Known as subintimal recanalization, this procedure can be very useful. There are some advantages to passing around the occlusion, rather than punching directly through it. The subintimal space is more likely to produce a smooth surface for blood flow versus the original lumen, which has remnants of the calcified plaque.

The technique has limited acceptance due to technical challenges of the procedure. Among those who perform subintimal recanalization, there is a technical failure rate of up to 30% due to the inability to reenter the distal true lumen at the specific desired location. Therefore, most clinicians will first try to cross the occlusion. If unsuccessful and if they enter the subintimal space, they will try to reenter the true lumen. If they cannot reenter after several minutes, they will abandon the case and schedule the patient for surgery.

During percutaneous transluminal recanalization, a variety of guidewires are used to pass the occlusion. If the occlusion is hard, a stiff wire is used to cross. Usually the proximal cap of the occlusion is the harder section, and if crossed, then crossing the rest of the occlusion is relative easy.

If during percutaneous extraluminal recanalization via the subintimal approach the true lumen cannot be reentered with guidewire manipulation, a true lumen reentry device must be used. Currently there are two specially designed reentry devices on the market. Published patent applications US20030236542, WO2006105244, US2003120195, and US2006094930 and U.S. Pat. No. 6,081,738 all describe reentry devices and methods, based on curved needle penetration, used with some type of rotational imaging system. PCT patent application PCT/IL2008/000449 describes a reentry balloon catheter that eliminates the needs for rotational orientation and operator direction via imaging guidance. This balloon catheter automatically bends its distal end in the direction of the true lumen. This device eliminates the need for a curved needle, and instead allows direct penetration with or without the support of a straight guidewire or hypotube.

SUMMARY OF THE INVENTION

The present invention describes a device for re-entry into the blood vessel's true lumen from the subintimal space between the layers of the blood vessel. The present invention provides inventive features further to those of PCT patent application PCT/IL2008/000449.

The present invention seeks to provide a device for reentry into a blood vessel's true lumen from an extraluminal or subintimal space of the vessel. The device eliminates the need for rotational orientation and operator direction via imaging guidance. In accordance with an embodiment of the present invention, a balloon catheter automatically bends the catheter's distal end in the direction of the true lumen. The device eliminates the need for a curved needle, and instead allows guidewire direct penetration with or without the support of a straight needle. The device of the invention can improve the technique of cardiologists, vascular surgeons, and radiologists in treating occlusions.

In accordance with an embodiment of the present invention, the occlusion is crossed by: 1) inserting the guidewire into the proximal vessel's true lumen, 2) pursuing guidewire vessel dissection into the subintimal space of the blood vessel close to the occluding plaque's proximal end, 3) advancing the guidewire through the subintimal space of the blood vessel distally to the plaque, 4) using the reentry balloon catheter of the invention to crack the intimal layer or stretch the intimal layer, 5) reentering the guidewire into the true lumen, 6) performing balloon angioplasty through the recanalized lumen, and 7) deploying one or more stents from the point of deflection into the subintimal space to the location of reentry into the true lumen.

The principle of operation of the subject device is based on balloon catheter technology. Specifically, the subject balloon catheter is inserted through the dissection, usually between the intimal and the adventitial layers of the blood vessel, over a guidewire until the balloon passed the distal end of the occlusion. The catheter of the invention includes a lumen for a guidewire passage.

The balloon used may be a small conical balloon. The balloon diameter may be similar or smaller than the true lumen of the blood vessel. The balloon can also have a ball shape or other similar elliptical shapes, in which its diameter is usually a few times the catheter's diameter, but preferably not more than the true lumen's diameter, and its length is short compared to common angioplasty balloons (i.e., not more than its diameter).

When the balloon is in place, the balloon is inflated to pressures of several atmospheres, thereby creating a space by pushing the surrounding tissues. Since the balloon is located subintimally between two layers of the blood vessel, and since the inflation pressure produces relatively high forces on the two tissue layers, the internal intima layer will bend or fold toward the true lumen. The balloon inflation will have a lesser effect on the external layer since the folding force is much higher than the stretching force, especially when folding toward a lumen. In other words, due to the differences in the elasticity of the vessel layers (i.e., the inner layer is more elastic than the outer layer), the catheter tip rotates in the direction of the true lumen, without the need for any orientation means or special visualization techniques.

Folding of the internal layer with minimal or no movement from the external layer will cause the catheter distal end to bend towards the true lumen. By creating a weaker section in the catheter at the proximal base of the balloon, the device leverages the asymmetrical forces and facilitates the tilt in the radial direction for punching through the internal layer back into the true lumen without the need for any imaging system for rotational orientation.

The penetration into the true lumen through the internal blood vessel layer can occur during balloon inflation (e.g., cracking of the intimal wall) and thereafter the guidewire, which may be stiff straight tip guidewire, can be advanced. Afterwards the catheter is withdrawn, and the guidewire remains for further percutaneous treatment. Alternatively, the balloon may bend and only stretch the intimal layer, and the guidewire is used to enter the true lumen.

The balloon of the invention may be mounted on the catheter or shaft with its distal neck bonded inside the balloon body, so as not to protrude distally beyond the balloon. Such a distal protrusion would fold and self-block when the balloon is flush with the intima. This would prevent advancing a guidewire or needle through the inner lumen of a balloon catheter for the purpose of crossing into the internal blood vessel layer.

As an alternative to direct guidewire penetration, a hypo tube that may be made from nitinol can be pre-inserted in the catheter lumen after the hypo tube is pre-cut to a needle shape at its distal end. After catheter distal end bending, the hypo tube is pushed slightly forward, penetrating into the true lumen, and then a guidewire is pushed through the hypo tube into the true lumen. Afterwards the hypo tube with the needle is pulled back into the catheter, and the catheter is withdrawn from the patient, leaving the guidewire in place.

The bending angle can be estimated based on the catheter point of bending at the plaque distal end and the balloon diameter.

In an embodiment of the present invention, the catheter has a weakened or softer small section near the balloon's proximal end, allowing it to bend easily with minimal resistance from the catheter's shaft. The location of this weak or less rigid section, together with the balloon diameter, will define the catheter's distal end bend angle.

In another embodiment of the present invention, the catheter has a third lumen, used for inserting second guidewire. This second wire will be used if the first wire distal end, inside the balloon, rotates over an angle which is not sufficient for the first wire to penetrate into the true lumen. The second wire is pushed until it is parallel to the deflated balloon. When the balloon is inflated the second wire will bend at a significant bending angle, which may be about twice the angle that the first wire deflects. The second wire bending angle is depended on the semi-compliant balloon inflation pressure and the balloon diameter. The second wire, which may be a stiff straight tip wire, is then pushed forward to penetrate the true lumen.

Using the second wire for penetration may require radial orientation. This can be done by using the two wires as radio-opaque markers, rotating the catheter until a maximal distance between the two wires is achieved, and the true lumen is beside the catheter at the same plane.

Crossing the occlusion may be done as follows: 1) inserting the first guidewire into the proximal vessel's true lumen, 2) pursuing guidewire vessel dissection into the subintimal space of the blood vessel close to the occluding plaque's proximal end, 3) advancing the guidewire through the sub-intimal space of the blood vessel distally to the plaque, 4) using the reentry balloon catheter of the invention to crack the intimal layer or stretch the intimal layer, 5) checking if the first guidewire reentered into the true lumen, if yes, proceeding to step 13, if not proceeding to next step 6) deflating the balloon, 7) inserting the second guidewire through the catheter third lumen, until parallel to the balloon, 8) making sure the catheter is at the desired location beside (the same plane) of the distal reentry point desired, 9) rotating the catheter until the distance between the two wires is maximal, 10) inflating the balloon, 11) increasing the balloon pressure until sufficient wire rotation is achieved, 12) pushing the second guidewire forward to penetrate the true lumen, and 13) performing balloon angioplasty through the re-canalized lumen, In another embodiment of the present invention, the catheter has only two lumens, the balloon lumen and the guidewire lumen, but the balloon lumen is not designed for guidewire passing through. In this configuration the balloon lumen can have a very small diameter, resulting in a small diameter of the whole catheter. The catheter has a groove at the balloon location, for free guidewire movement. The method for true lumen reentry from the sub-intimal space with this catheter is only by deflecting the guidewire towards the true lumen by inflating the balloon. This method may include radial orientation of the guidewire to be on the true lumen side and to point towards the true lumen while deflected by the balloon.

BRIEF DESCRIPTION OF THE DRAWINGS

The present invention will be understood and appreciated more fully from the following detailed description taken in conjunction with the drawings in which.

DETAILED DESCRIPTION OF THE INVENTION

The present invention describes a device for re-entry into the blood vessel's true lumen from the subintimal space between the layers of the blood vessel. The present invention provides inventive features further to those of PCT patent application PCT/IL2008/000449, the disclosure of which is incorporated herein by reference.

The present invention eliminates the needs to steer a catheter rotationally with the assistance of an imaging system in order to orient a needle, guidewire, or other tool towards the true lumen for puncturing the intima layer. The catheter automatically bends its distal end in the direction of the true lumen without operator guidance and/or imaging. The device of the invention eliminates the need for curved needle, and allows direct guidewire penetration with or without the support of a straight needle.

Figure 1:
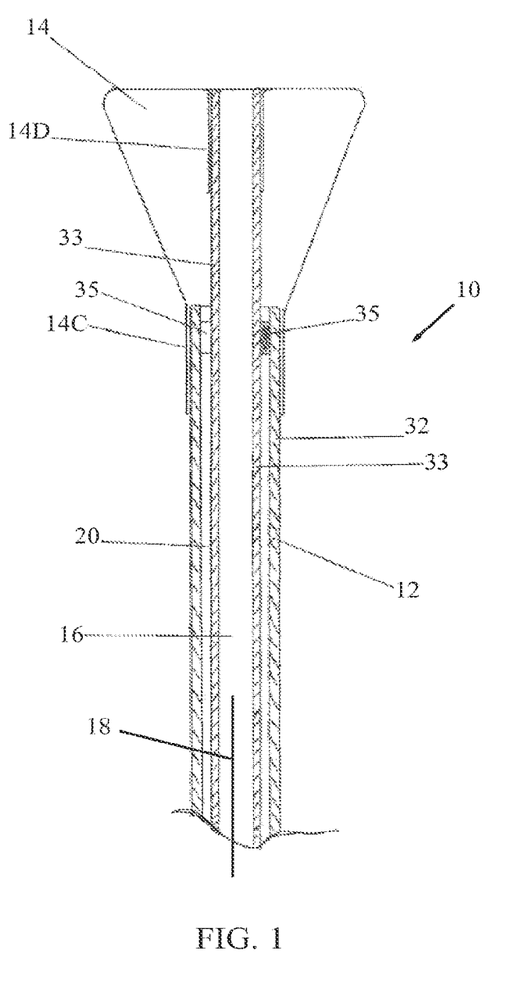
FIG. 1 is a simplified illustration of a lumen reentry device, constructed and operative in accordance with an embodiment of the present invention.

Reference is now made to FIG. 1, which illustrates a lumen reentry device 10, constructed and operative in accordance with an embodiment of the present invention. Device 10 is similar in construction to the device described in PCT patent application PCT/IL2008/000449. Device 10 includes a catheter 12 which has a balloon 14 disposed at a distal end thereof. The distal end of catheter 12 protrudes only slightly, or does not protrude at all, beyond balloon 14. Catheter 12 is formed with a first lumen 16 through balloon 14 for passing therethrough a guidewire 18, and a second lumen 20 for inflation and deflation of balloon 14.

Catheter 12 may be fabricated from polyethylene, polyurethane, PEBAX (polyether block amide from Arkema), nylon or other polymers known in the art. The catheter shaft can also be made from polymers reinforced with metal wires braid or springs, as is known in the art.

Balloon 14 may be fabricated from polyurethane, silicon, PET (polyethylene terephthalate), and other suitable polymers known in the art. Balloon 14 is preferably, but not necessarily, cone-shaped.

In accordance with an embodiment of the present invention, catheter 12 has a weakened or softer small section 22 (bending section 22), located either inside or outside near the proximal end of the balloon 14, allowing balloon 14 to bend easily with minimal resistance from the catheter shaft. Bending section 22 can be a small section having a smaller wall thickness or a section lacking metal wire springs or braid, making it softer and easy to bend or rotate. The position of this weak or less rigid section, together with the balloon diameter, defines the catheter's distal end bend angle.

In accordance with an embodiment of the invention, catheter 12 is made from two tubes, one inside the other, a softer internal tube 33 which extends distally to a harder external tube 32. This construction facilitates balloon bending, and the distal end of the harder external tube 32 defines the balloon bending point.

The use of a soft internal tube 33 in catheter 12 might cause too much strain during balloon inflation due to the axial force on the internal tube from the inflated balloon. This might cause a failure of distal balloon's neck bonding as the internal tube elongates and the inverted balloon's distal neck can peel away from it.

In accordance with an embodiment of the invention, a strain-reducing element is mounted in catheter 12 that reduces strain on a distal portion of balloon 14 during inflation of balloon 14, examples of which are now described.

In order to prevent or significantly decrease such elongation, the internal and external tubes can be bonded one to the other close to the external tube distal end, shortening the effective length of the internal tube on which axial force is applied, preventing the above peeling effect. The bonding between the two tubes can be done with UV glue, as long as the glue does not block the balloon inflation lumen 20 between the two tubes. Alternatively a C ring 35 made from a polymer or metal, can be used to connect the distal sections of the two tubes together, by bonding the C ring to both tubes. The space in the C ring 35 prevents blockage of the balloon inflation lumen 20.

Figure 2:
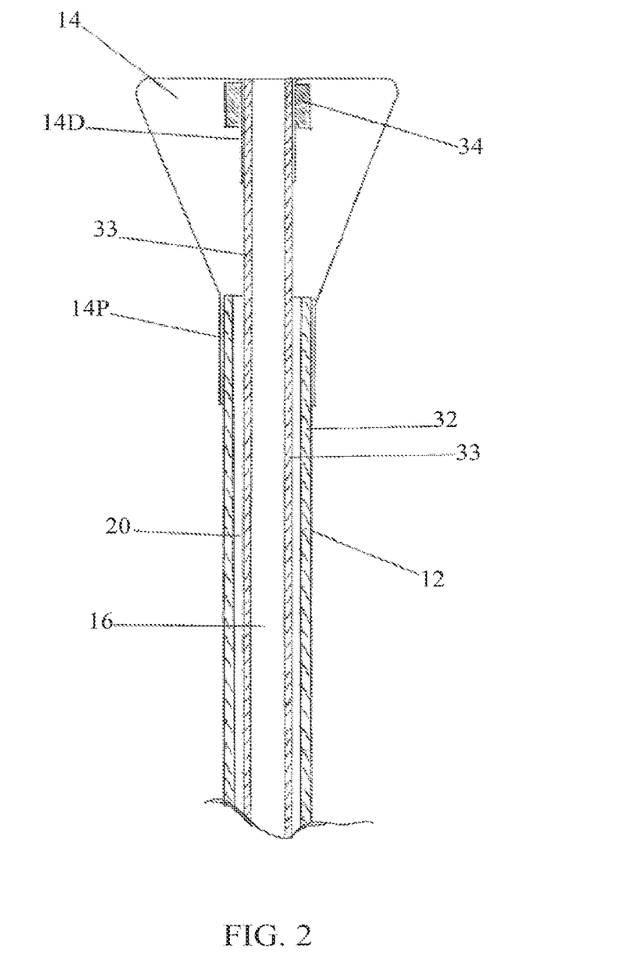
FIG. 2 is a simplified illustration of the lumen reentry device, alternatively or additionally, with a ring used to further increase the bonding strength of an inverted distal neck of a balloon of the lumen reentry device, in accordance with an embodiment of the present invention.

Reference is now made to FIG. 2. Alternatively or additionally, a ring 34, made from plastic or from radiopaque materials, such as titanium and iridium alloy, can be used to further increase the bonding strength of the inverted distal neck 14D of balloon 14. The inverted neck 14D is exposed to peeling forces caused by both radial and axial forces due to the balloon inflation. Ring 34, mounted at the distal end of internal tube 33 and the distal end of balloon 14, prevents such peeling of the inverted distal neck 14D from the internal tube 33.

Figure 3:
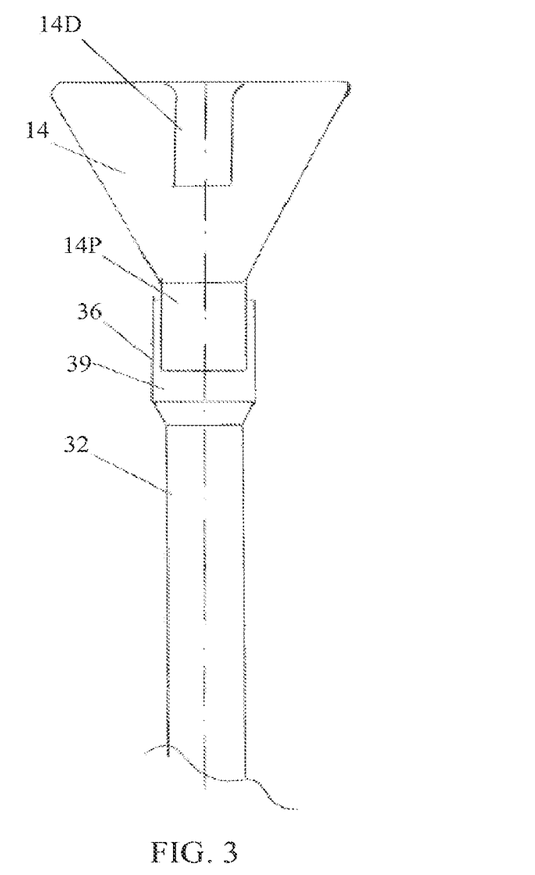
FIG. 3 is a simplified illustration of a hydraulic sealing design in accordance with an embodiment of the present invention.
Figure 4:
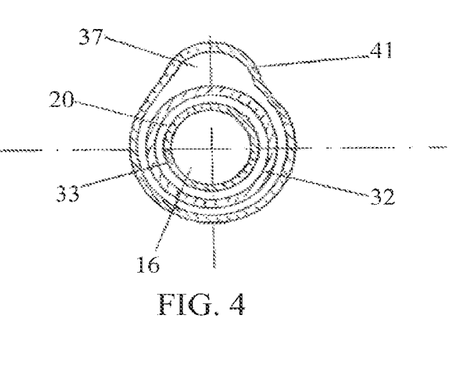
FIGS. 4, 5, 6A and 6B are simplified illustrations of a catheter with a third lumen used for inserting a second guidewire, constructed and operative in accordance with another embodiment of the present invention.

Reference is now made to FIG. 3. In another embodiment of the invention, in order to increase the attachment strength of the proximal neck 14P of balloon 14 to the external tube 32, a hydraulic sealing design can be used. A short flare 36 is produced at the distal end 39 of external tube 32, such as by pushing the tube against a hot mandrel, having a slightly larger diameter and length than the balloon's proximal neck 14P. The balloon's proximal neck 14P is then inserted into flare 36 and bonded. During balloon inflation, the softer balloon proximal neck 14P abuts against the harder flare 36 of external tube 32. The higher the pressure, the more the proximal neck 14P is pushed towards flare 36.

Figure 5:
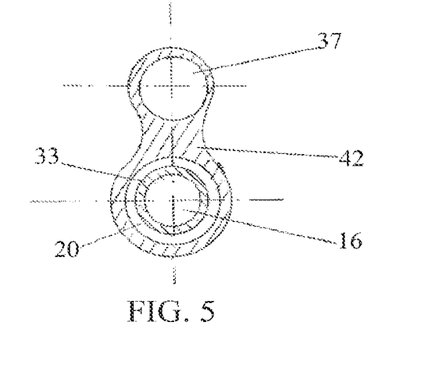
Figure 6A:
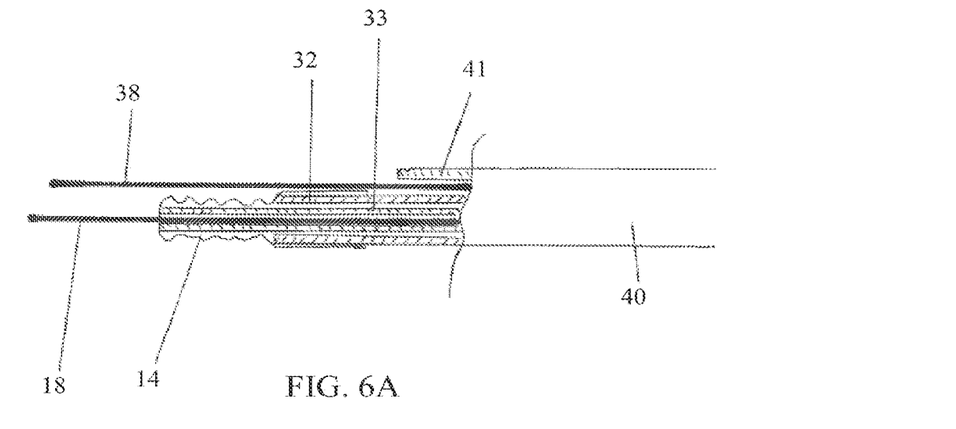
Figure 6B:
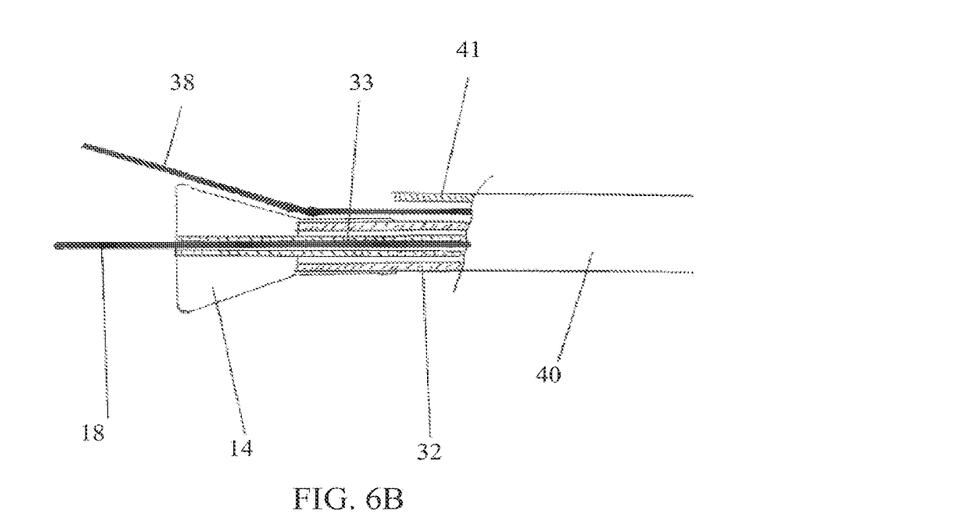

Reference is now made to FIGS. 4, 5, 6A and 6B. In accordance with another embodiment of the present invention, a catheter 40 has a third lumen 37 (FIGS. 4-5), used for inserting a second guidewire 38 (FIGS. 6A-6B). Third lumen 37 can be formed by placing an additional specially shaped tube 41 over external tube 32 (FIG. 4), wherein third lumen 37 is a bulbous protrusion of tube 41, or by making the external tube 32 into a double lumen tube 42 (FIG. 5). When using tube 41 for third lumen 37, tube 41 ends near the proximal end of balloon 14. When using double lumen tube 42, tube 42 can end near the proximal end of balloon 11, but alternatively, third lumen 37 may end near the distal end of balloon 14 by extending a portion of tube 42 over a portion of balloon 14, thereby providing better protection for balloon 14.

Second guidewire 38 can be used if the distal end of the first guidewire 18, located inside balloon 14, rotates at an angle which is not sufficient for first guidewire 18 to penetrate into the true lumen. The second guidewire 38 is pushed until it is parallel or even slightly proximal to the deflated balloon 14 (FIG. 6A). When balloon 14 is inflated, second guidewire 38 bends at a bending angle, which is about twice the angle of deflection of the first guidewire 18 (FIG. 6B). The bending angle of the second guidewire 38 depends on the inflation pressure and diameter of balloon 14, and also on the location of the bending point of second guidewire 38, which is the distal end of third lumen 37. Second guidewire 38, which may be a stiff straight tip wire, is then pushed forward to penetrate the true lumen. Preferably after second guidewire 38 penetrates the true lumen, balloon 14 is deflated, to allow easy and safe further insertion of second guidewire 38 into the true lumen.

Using second guidewire 38 for penetration generally requires two views of fluoroscopy radial orientation. Such orientation can be done using the two wires 18 and 38 as radiopaque markers, rotating catheter 40 until the maximum distance between the two wires is achieved, and the true lumen is beside catheter 40.

Figure 7:
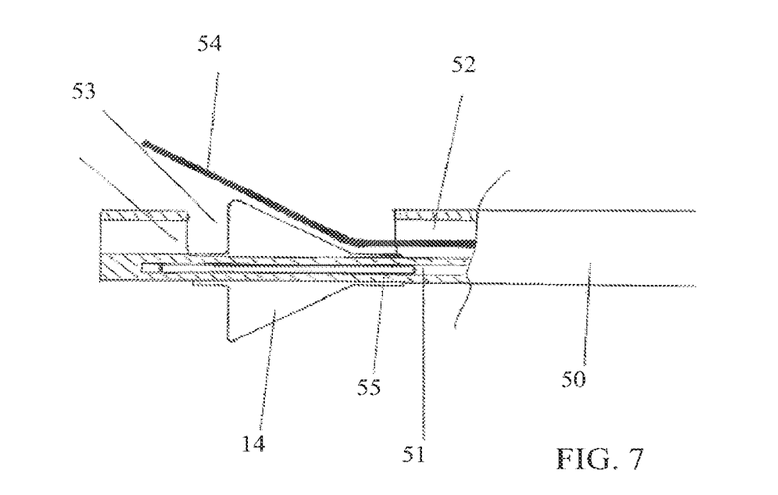
FIG. 7 is a simplified illustration of a catheter that has two lumens, a balloon lumen and a guidewire lumen, constructed and operative in accordance with another embodiment of the present invention.

Crossing the occlusion may be done as follows: 1) inserting the first guidewire into the proximal vessel's true lumen, 2) pursuing guidewire vessel dissection into the subintimal space of the blood vessel close to the occluding plaque's proximal end, 3) advancing the guidewire through the subintimal space of the blood vessel distally to the plaque, 4) using the reentry balloon catheter of the invention to crack the intimal layer or stretch the intimal layer, 5) checking if the first guidewire reentered into the true lumen, if yes, proceeding to step 13, if not proceeding to next step 6) deflating the balloon, 7) inserting the second guidewire through the catheter third lumen, until parallel to the balloon, 8) making sure the catheter is at the desired location beside (the same plane) of the distal reentry point desired, 9) rotating the catheter until the distance between the two wires is maximal, 10) inflating the balloon, 11) increasing the balloon pressure until sufficient wire rotation is achieved, 12) pushing the second guidewire forward to penetrate the true lumen, and 13) performing balloon angioplasty through the re-canalized lumen, Reference is now made to FIG. 7. In another embodiment of the present invention, a catheter 50 has two lumens, a balloon lumen 51 and a guidewire lumen 52. The balloon lumen 51 is not designed for a guidewire to pass therethrough. In this configuration the balloon lumen 51 can have a very small diameter, resulting in a very small diameter of the whole catheter 50. Catheter 50 has a groove 53 proximal and distal to the balloon 14, for free movement of a guidewire 54 that passes through groove 53. Reentering from the sub-intimal space with catheter 50 is carried out by deflecting guidewire 54 towards the true lumen by inflating balloon 14. This method requires radial orientation of guidewire 54 to be on the true lumen side and to point towards the true lumen while deflected by balloon 14. A bar or tube 55, made of metal or other hard material, can be added inside the balloon lumen 51 to add structural rigidity to the catheter distal end.

Reference is now made to FIGS. 8-11, which illustrate a method for thermal bonding of the inverted balloon neck of catheter 12, in accordance with an embodiment of the present invention. As is described more in detail below, the method includes heating through the internal catheter shaft lumen, while applying internal pressure to attach the shaft external surface to the inverted balloon neck. (It is noted that the balloon in catheters 40 and 50 may have a distal tip that protrudes distally from the balloon, and thus do not need to be manufactured this way.)

Figure 8:
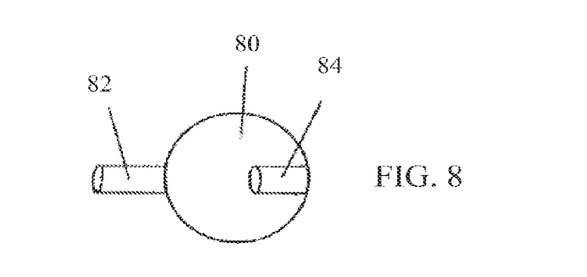
FIGS. 8-11 are simplified illustrations of a method for thermal bonding of the inverted balloon neck of the catheter, in accordance with an embodiment of the present invention.

As seen in FIG. 8, Balloon 80 has a cylindrical or elliptical shape, and includes a proximal neck 82 and a distal inverted neck 84 which protrude from both sides of the main body of the balloon. The internal surface of inverted neck 84, which before the neck inversion was the outer neck surface, and its diameter usually change and twist during the neck inversion process, which is done by applying mechanical force on the balloon neck.

Figure 9:
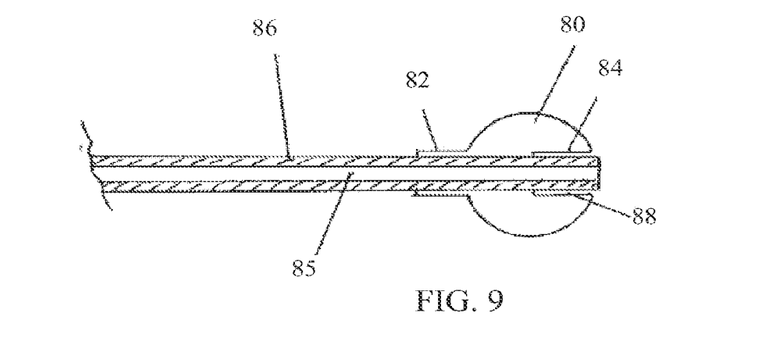

As seen in FIG. 9, balloon 80 is mounted on a shaft 86. There may be some a gap 88 (space/tolerance) between the external contour of shaft 86 and the internal diameter of inverted neck 84, to allow pushing balloon 80 over shaft 86. Gap 88 is acceptable for gluing, but must be eliminated if thermal bonding is desired, because there must be good contact between the shaft and balloon inverted neck for thermal bonding.

Figure 10:
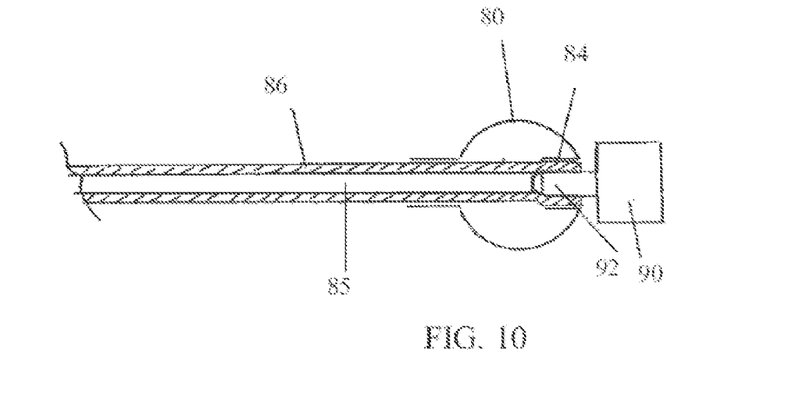

As seen in FIG. 10, a probe 90, which has a protrusion 92, is pushed into the hollow 85 of shaft 86 at the area to be bonded. Protrusion 92 has a larger diameter than the hollow 85 of shaft 86, large enough to expand the polymeric shaft material and eliminate the gap between shaft 86 and balloon inverted neck 84. Probe 90 is then heated to a desired temperature, usually in the range of 170 to 300.degree. C., for up to 60 seconds, until good thermal bonding of the two polymers is achieved. Protrusion 92 may be chamfered for easy insertion into shaft 86 of the catheter. Probe 90 may be made from metal, and preferably a good heat-conductive metal like aluminum or brass.

Figure 11:
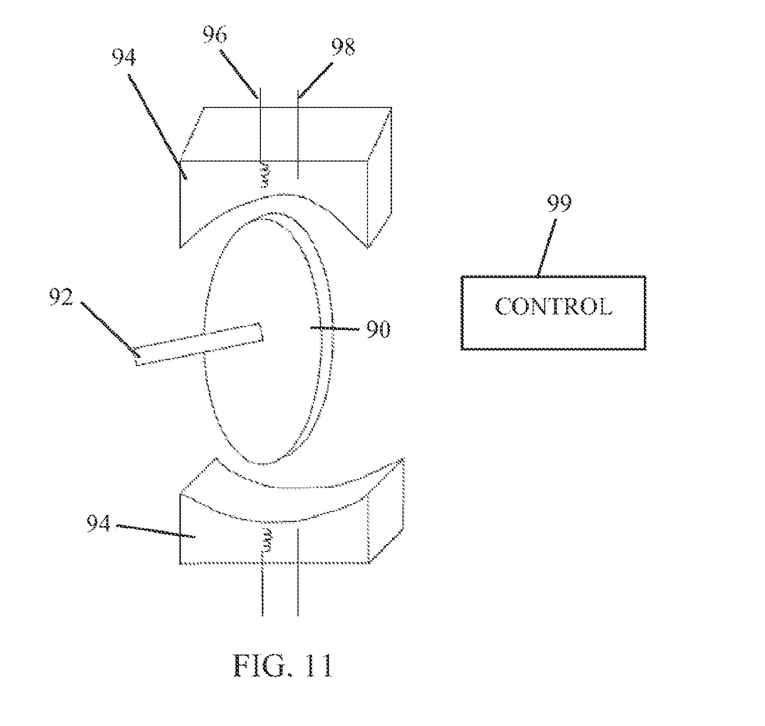

As seen in FIG. 11, the heating machine may have two metal heating clamps 94. Each clamp 94 includes a heating element 96 and thermocouple 98, all connected to a controller 99, that controls the clamp temperature and the probe clamping time.

What is claimed is:

1. A lumen re-entry device, comprising:
an elongate catheter shaft;
an inflatable balloon mounted on a distal region of the elongate catheter shaft;
the elongate catheter shaft including a first lumen in fluid communication with an interior of the inflatable balloon;
the elongate catheter shaft including an inner surface defining a second lumen having a distal opening positioned proximal of the inflatable balloon; and
an elongate member directly facing the inner surface of the second lumen with no intervening structure therebetween, the elongate member being slidably extendable through the second lumen to extend in a direction parallel to a longitudinal axis of the elongate catheter shaft as the elongate member exits out the distal opening of the second lumen and extends alongside a proximal neck of the inflatable balloon when the inflatable balloon is inflated;
wherein a body portion of the inflatable balloon is configured to deflect a distal end portion of the elongate member upon inflation of the inflatable balloon.

2. The lumen re-entry device of claim 1, wherein the elongate member is a guidewire.

3. The lumen re-entry device of claim 1, wherein the elongate catheter shaft further includes a third lumen having a distal opening positioned distal of the inflatable balloon.

4. The lumen re-entry device of claim 3, wherein the third lumen is a guidewire lumen.

5. The lumen re-entry device of claim 1, wherein the elongate catheter shaft includes a first tubular member secured to the proximal neck of the inflatable balloon and a second tubular member secured to a distal neck of the inflatable balloon.

6. The lumen re-entry device of claim 5, wherein the second tubular member has a distal end located distal of a distal end of the first tubular member.

7. The lumen re-entry device of claim 5, wherein the second tubular member extends through a lumen of the first tubular member.

8. The lumen re-entry device of claim 1, wherein the body portion of the inflatable balloon extends from the proximal neck to a distal neck, wherein the body portion tapers radially outward in a distal direction in an inflated state.

9. The lumen re-entry device of claim 8, wherein the inflatable balloon is a conically-shaped balloon.

10. The lumen re-entry device of claim 1, wherein the inflatable balloon includes an inverted distal neck secured to a distal end of the elongate catheter shaft.

11. A lumen re-entry device, comprising:
an elongate catheter shaft having a first lumen and a second lumen;
an inflatable balloon having a proximal neck mounted on a distal region of the elongate catheter shaft;
the first lumen being in fluid communication with an interior of the inflatable balloon and the second lumen having a distal opening located proximal of the inflatable balloon; and
an elongate member slidable relative to the elongate catheter shaft, the elongate member configured to extend from the distal opening of the second lumen in a direction parallel to a longitudinal axis of the elongate catheter shaft alongside the proximal neck of the inflatable balloon when the inflatable balloon is inflated, the elongate member configured to be positionable exterior of and in direct contact with a proximal conical outer surface of the inflatable balloon;
wherein the inflatable balloon is configured to deflect a distal end portion of the elongate member upon inflation of the inflatable balloon.

12. The lumen re-entry device of claim 11, wherein the elongate member is a guidewire advanceable in direct contact with an outer surface of the inflatable balloon.

13. The lumen re-entry device of claim 11, wherein the inflatable balloon includes a body portion extending from the proximal neck to a distal neck, wherein the body portion tapers radially outward in a distal direction in an inflated state.

14. The lumen re-entry device of claim 13, wherein the inflatable balloon is a conically-shaped balloon.

15. The lumen re-entry device of claim 11, wherein the inflatable balloon includes an inverted distal neck secured to a distal end of the elongate catheter shaft.

16. The lumen re-entry device of claim 11, wherein the elongate catheter shaft includes a tubular member extending through the inflatable balloon.

17. The lumen re-entry device of claim 16, wherein the tubular member defines a third lumen extending to a distal opening distal of the inflatable balloon.

18. The lumen re-entry device of claim 16, wherein the inflatable balloon includes an inverted distal neck secured to a distal end of the tubular member.

19. The lumen re-entry device of claim 11, wherein the elongate member is configured to extend though the second lumen and exit out the distal opening of the second lumen.

20. The lumen re-entry device of claim 11, wherein the elongate catheter shaft includes a first tubular member secured to the proximal neck of the inflatable balloon and a second tubular member secured to a distal neck of the inflatable balloon.

* * * * *